(12) United States Patent
Burioni

(10) Patent No.: US 7,727,529 B2
(45) Date of Patent: Jun. 1, 2010

(54) HUMAN MONOCLONAL ANTIBODY FAB FRAGMENTS DIRECTED AGAINST HCV E2 GLYCOPROTEIN AND ENDOWED WITH IN VITRO NEUTRALIZING ACTIVITY

(75) Inventor: Roberto Burioni, Rimini (IT)

(73) Assignee: General Antibodies and Biotechnologies S.R.L, San Marion (IT)

( * ) Notice: Subject to any disclaimer, the term of this patent is extended or adjusted under 35 U.S.C. 154(b) by 0 days.

(21) Appl. No.: 12/128,344

(22) Filed: May 28, 2008

(65) Prior Publication Data

US 2008/0241162 A1    Oct. 2, 2008

Related U.S. Application Data

(63) Continuation of application No. 10/502,307, filed as application No. PCT/IT03/00032 on Jan. 29, 2003, now abandoned.

(30) Foreign Application Priority Data

Jan. 30, 2002    (IT) ......................... RM2002A0049

(51) Int. Cl.
*A61K 39/395*    (2006.01)
*A61K 39/42*    (2006.01)
*C07K 16/00*    (2006.01)
*C12P 21/08*    (2006.01)

(52) U.S. Cl. .............. 424/149.1; 424/133.1; 424/141.1; 424/147.1; 530/387.1; 530/387.3; 530/388.1; 530/388.3

(58) Field of Classification Search ....................... None
See application file for complete search history.

(56) References Cited

U.S. PATENT DOCUMENTS 7,091,324 B2 *   8/2006   Foung et al. ............. 530/388.3

FOREIGN PATENT DOCUMENTS

WO    WO 00/05266    2/2000
WO    WO 02/005560 A2    7/2002

OTHER PUBLICATIONS

Burioni et al., "Dissection of human humoral immune response against hepatitis C virus E2 glycoprotein by repertoire cloning and generation of recombinant fab fragments," vol. 28 No. 3, pp. 810-814 (Sep. 1998).*
Habersetzer et al., "Characterization of human monoclonal antibodies specific to the hepatitis C virus glycoprotein E2 with in vitro binding neutralization properties," Virology, vol. 249 No. 1, pp. 32-41 (Sep. 1998).*
Poul et al., "Design of cassette baculovirus vectors for the production of therapeutic antibodies in insect cells," Immunotechnology, vol. 1 No. 3-4, pp. 189-196 (Dec. 1995).*
Bretner, Maria, Existing and future therapeutic options for hepatitis C virus infection, Acta Biochimica polonica, vol. 52 No. 1, pp. 57-70 (2005).*
Leroux-Roels, Geert, Development of prophylactic and therapeutic vaccines against hepatitis C virus, Expert Review of Vaccines, vol. 4 No. 3, pp. 351-371 (Jun. 2005).*
Perotti et al., "Identification of a Broadly Cross-Reacting and Neutralizing Human Monoclonal Antibody Directed against the Hepatitis C Virus E2 Protein," Journal of Virology, vol. 82 No. 2, pp. 1047-1052 (Jan. 2008).*

Eren et al., "Preclinical Evaluation of Two Neutralizing Human Monoclonal Antibodies against Hepatitis C Virus (HCV): a Potential Treatment to Prevent HCV Reinfection in Liver Transplant Patients," Journal of Virology, vol. 80 No. 6, pp. 2654-2664 (Mar. 2006).*
Bugli et al., "Mapping B-Cell Epitopes of Hepatitis C Virus E2 Glycoprotein Using Human Monoclonal Antibodies from Phage Display Libraries," Journal of Virology, vol. 75 No. 20, pp. 9986-9990 ( Oct. 2001).*
PCT International Search Report for Burioni, Roberto, Int'l Application No. PCT/IT03/00032, Filed Jan. 29, 2003, Dated Aug. 6, 2003.
Allander, et al., "Recombinant Human Monoclonal Antibodies against Different Conformational Epitopes of the E2 Envelope Glycoprotein of Hepatitis C Virus That Inhibit Its Interaction with CD81." Journal of General Virology, vol. 81, 2451-2459 (2000).
Burioni, et al., "Nonneutralizing Human Antibody Fragments against Hepatitis C Virus E2 Glycoprotein Modulate Neutralization of Binding Activity of Human Recombinant Fabs." Virology, vol. 288, 29-30 (2001).
Dietzschold et al., "Delineation of putative mechanisms involved in antibody-mediated clearance of rabies virus from the central nervous system", Proc. Natl. Acad. Sci., USA, vol. 89, pp. 7252-7256 (1992).
Fujinami et al, "Survival of Athymic (nu/nu) Mice after Theiler's Murine Encephalomyelitis Virus Infection by Passive Administration of Neutralizing Monoclonal Antibody", Journal of Virology, vol. 63, No. 5, pp. 2081-2087 (1989).
Lavillette et al., "Human Serum Facilitates Hepatitis C Virus Infection, and Neutralizing Responses Inversely Correlate with Viral Replication Kinetics at the Acute Phase of Hepatitis C Virus Infection", Journal of Virology, vol. 79, No. 10, pp. 6023-6034 (2004).
Law et al., "Broadly neutralizing antibodies protect against hepatitis C virus quasispecies challenge", Nature Publishing Group, pp. 1-3 (2007).
Logvinoff et al., "Neutralizing antibody response during acute and chronic hepatitis C virus infection", PNAS, vol. 101, No. 27, pp. 10149-10154 (2004).
Moore et al., "HIV-1 neutralizing antibodies: How fill is the bottle", Nature America Inc, vol. 5, No. 2, pp. 142-144, (1999).
Rosa D., et al., "A Quantitative Test to Estimate Neutralizing Antibodies to the Hepatitis C Virus: Cytofluorimentric Assessment of the Envelope Glycoprotien 2 Binding to Target Cell." Proceedings of the National Academy of Sciences of USA, National Academy of Science. Washington, US, vol. 93, No. 3 (Mar. 1, 1996).
Virgin et al., "Antibody Protects against Lethal Infection with the Neurally Spreading Reovirus Type 3 (Dearing)", Journal of Virology, vol. 62, No. 12, pp. 4594-4604 (1988).
Wohlfart, Claes, "Neutralization of Adenoviruses: Kinetics, Stoichiometry, and Mechanisms", Journal of Virology, vol. 62, No. 7, pp. 2321-2328 (1988).
U.S Office Action for Burioni., U.S. Appl. No. 10/502,307, filed Jul. 22, 2004, Dated Mar. 2, 2007.
U.S Office Action for Burioni., U.S. Appl. No. 10/502,307, filed Jul. 22, 2004, Dated Apr. 30, 2008.

* cited by examiner

*Primary Examiner*—Zachariah Lucas
(74) *Attorney, Agent, or Firm*—Law Offices of Albert Wai-Kit Chan, PLLC

(57) ABSTRACT

The invention refers to a human antibody, or its functional fragments, directed against the HCV E2 glycoprotein, able to have a neutralizing activity in vivo; a composition for anti-HCV therapy comprising in a therapeutically effective amount the antibody; a composition for topical use in gel, creme, ointment and ovule formulations; the use of the antibody for validating anti-HCV vaccines.

15 Claims, 7 Drawing Sheets

HUMAN MONOCLONAL ANTIBODY FAB FRAGMENTS DIRECTED AGAINST HCV E2 GLYCOPROTEIN AND ENDOWED WITH IN VITRO NEUTRALIZING ACTIVITY

This application is a continuation of U.S. Ser. No. 10/502,307, now abandoned, filed Jul. 22, 2004, which is the National Stage of International Application No. PCT/IT2003/00032 filed Jan. 29, 2003, which claims priority of Italian Application No. RM2002A000049, filed Jan. 30, 2002, the entire disclosures of the preceding applications are incorporated by reference herein in item entireties.

The invention concerns human monoclonal antibody Fab fragments directed against HCV E2 glycoprotein and endowed with in vitro neutralizing activity. Hepatitis C virus (VCV) infects about 4% of the world population (World Health Organization, 1999). Over 80% of subjects coming into contact with this pathogen develop a chronic infection as the host immune response is unable to eradicate the infection, with the risk of severe liver diseases such as chronic hepatitis, cirrhosis and liver cell carcinoma [1, 2].

Treatment of chronic infection is based on combined therapy with interferon and ribavirin, which is extremely costly causes major side effects and is moderately effective (only 1 patient in 4 obtains long-term results) [3, 4]. The viral infection does not provide immune protection. This fact, together with the virus's high variability in antigenic structure recognized by the immune system, has hindered the development of an effective serum therapy and vaccines to protect individuals against HCV infection. It is therefore clear that new antiviral strategies are strongly needed.

The author has cloned the genes coding for a large number of human Fabs antibody fragments directed against one of the HCV proteins, the external E2 glycoprotein, considered the most important target for immune protective response [5]. However, the evaluation of the biological activity of these antibody fragments is not simple, as no reliable in vitro systems are available to determine the neutralizing activity against HCV. Hence, the author has only evaluated and described the variable ability of different Fabs to inhibit the binding of protein E2 to the target cell, without demonstrating a correlation between this activity and the neutralizing activity of the sera [5].

In a previous work, Burioni et al. (2001) [6], showed that some anti-E2 antibodies produced by HCV-infected patients have a negative effect, rendering the virus less sensitive to host immune response, probably due to its binding to the E2 antigen and to modifications of its conformation [6]. This could explain why high anti-E2 antibody titers are not directly correlated with protection against HCV infection.

Bugli et al., 2001 [7] generated a map of E2 protein epitopes that can bind in vitro the panel of anti-E2 human Fabs, showing four discrete regions against which immune response is directed (FIG. 2) [7]. The presence of antibodies directed against one or more of these regions in the serum of chronically infected patients could be associated with complications, reduced effectiveness of treatment and a different prognosis. It is therefore evident that there is a need for a method to determine antibodies in a biological fluid directed against different epitopes of the HCV E2 protein. An embodiment of the present invention provides this method.

The authors of the invention have also evaluated the neutralizing activity of various anti-E2 antibodies in a system of viral pseudotypes, i.e. viruses externally identical to HCV but, after entering the target cells which are able to produce a protein that produces fluorescence [8]. By revealing the presence or absence of fluorescence in the cells, the method provides a direct measure of the in vivo neutralizing activity of anti-E2 antibodies directed against different epitopes.

Unexpectedly, the authors found that two of the assayed antibodies, e137 and e301, can neutralize the virus at concentrations obtainable with a single parenteral administration of an antibody preparation; two other antibodies had no neutralizing activity and one was even able to promote viral infection.

The development of the method of titering different antibody populations in a patient represents a valuable diagnostic and prognostic instrument with the potential to distinguish between affected subjects at risk for developing severe complications and those with a more favorable prognosis. In this latter group, this method would eliminate the need to administer a largely ineffective treatment that is also associated with severe side effects, while providing a considerable reduction in costs.

As the E2 epitopes, so identified, are not reproducible by synthesizing synthetic peptides [5], the method represents the only way to determine the amount of antibodies against the different parts of the protein E2, with correlated clinical and epidemiological data.

The identification of anti-E2 antibodies in the human Fabs format with a good neutralizing ability permits their large-scale production and use as a medication in anti-HCV treatment, or as a preventive agent in topical form to inhibit viral transmission to subjects at risk (couples with discordant HCV state, individuals subject to occupational exposure, etc.).

The antibodies of the invention can be advantageously used to evaluate in vitro candidate molecules for anti-HCV vaccines, i.e. able to stimulate neutralizing antibodies but not ineffective or negative antibodies.

The availability of neutralizing human antibodies able to recognize a broad spectrum of viruses could be crucial in the production of artificial vaccines. The neutralizing antibodies described in this document can be used as a template for the development of vaccines (made from peptides or anti-idiotype antibodies) able to stimulate a neutralizing cross-reactive response.

The object of this invention is a human antibody, or its functional fragments, against the HCV E2 protein, endowed with an in vivo neutralizing activity.

In a particular embodiment, the antibody of the invention is the antibody e137, which is characterized by the following amino acid sequences of the variable part of the heavy and light chains:

```
e 137 Heavy chain (HC) (SEQ ID NO: 7)
LLEQSGSEVKVPGSSLKVSCKTSGGTFSTYTFSWVRQAPGQGLEWMG

GITPIIGIANYARNFQDRVTITADESTSTVYMEVRRLRSEDTAVYYCAKT

SEVTATRGRTFFYSAMDVWGQGT e 137 Light chain (LC) (SEQ ID NO: 8)
MAELTQSPSFLSASVGDRVTITCRASQGISNYLAWYQQKPGKAPKLLIYA

ASTLQSGVPSRFSGSGSWTEFTLTISRLQPEDFATYYCQHLNTYPWTFG

QGT
```

In an alternative embodiment, the antibody of the invention is the antibody e301, which is characterized by the following amino acid sequences of the variable part of the heavy and light chains:

```
e 301 Heavy chain (HC) (SEQ ID NO: 9)
LLEQSGSEVKKPGSSVRVSCTTSGGTLSDYGFNWLRQAPGQGPEWMG

GIIPLFRRTTYGQKFQGRLTITADESTGATYMELSSLRSDDTAVYYCARE

KVSVLTGGKSLHYFEYWGKGT e 301 Light chain (LC) (SEQ ID NO: 10)
MAELTQSPATLSVSPGERATLSCRASQSVSSRLAWYQQKRGQAPSLLIY

DTSSRATGVPARFSASGSGTQFTLTISSLQSEDFALYYCQQYNDWPSTF

GQGT
```

A further object of the invention is a composition for anti-HCV therapy comprising in a therapeutically effective amount at least one of the antibodies of the invention. Preferably, the composition is supplied in purified form for parenteral use or in another formulation for topical use as a gel, creme, ointment, ovule, with excipients known to experts in the field. A further object of the invention is a nucleic acid coding for each of the antibodies of the invention. Advantageously, the nucleic acid can be contained in an expression vector which can effectively express the antibody of the invention in prokaryote or also in eukaryote cells. In a preferred form, the recombinant vector also contains a nucleotide sequence coding for a signal peptide which is substantially contiguous with the coding sequence for the antibody of the invention, and is able to export the antibody out of the cell environment.

A further object of the invention is the use of the recombinant vector as described in gene therapy.

The invention is described below in experimental examples, not limiting the invention itself, in reference to the following figures:

EXAMPLE 1

Materials and Methods

Anti-HCV Fabs and Full-Size IgG1 Production

Generation, purification and characterization of the anti-HCV/E2 Fabs have been described elsewhere [5]. FLAG-Fabs (Fabs labeled with a FLAG epitope fused at the carboxy-terminal of the heavy chain fragment with a pentapeptide bridge) were constructed and purified as described elsewhere [6]. Validation and standardization of the assay were performed using Fab-coding genes to construct full-size human monoclonal antibodies (HuMabs), which were inserted in an appropriate eukaryotic vector for subsequent production in transfected cells [9]. The HuMabs present in the culture supernatant were purified by immunoaffinity as described [10] and purity-checked by PAGE. The amount of human antibody was assayed by a sandwich immunoassay. All antibodies and Fabs were stored at −70° C. until use.

Sera and Specimens

Sera obtained from healthy donors and HCV-positive patients were analyzed using commercial diagnostic kits (Ortho, Raritan, N.J.) following standard procedures. For the preparation of mock specimens with known amounts of antibodies directed against a given epitope, HCV-negative sera were spiked with concentrated purified HuMabs in PBS and treated exactly like the positive and negative sera.

Design of Fab Inhibition Titer (FIT) Assay

Figure 1:
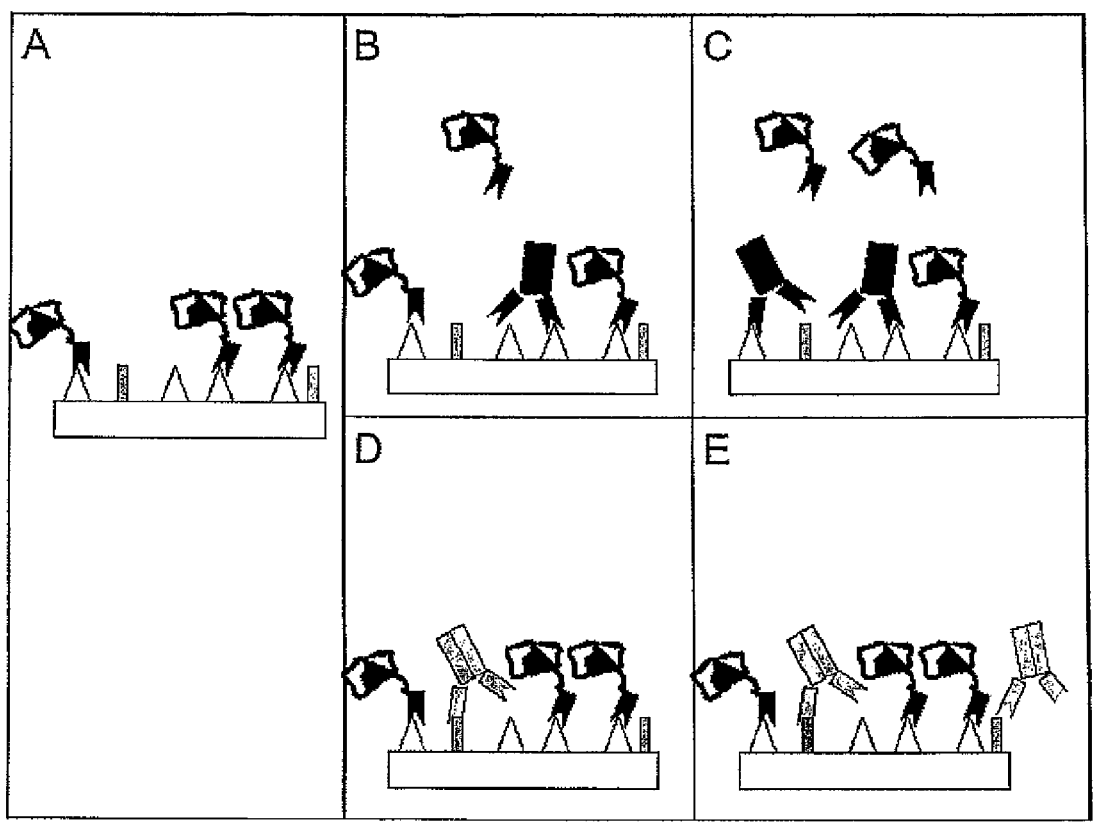
FIG. 1 FIT: THEORETICAL BASIS. Panel A shows the binding of a Fab-FLAG to its epitopes without competitors. Using the same concentration of Fab present in (A), preincubation of the antigen with the patient's serum permits quantitative analysis of antibodies directed against the epitope recognized by the Fab in the serum. In panels B and C, the bound antibodies, as they compete with Fab, proportionately diminish the amount bound compared with panel A. In panels D and E, the presence of antibodies not directed against the specific epitope does not minimally influence Fab binding.

The purpose of this assay is to assess the ability of sera to inhibit the binding of a labeled Fab to its epitope, thus obtaining an indirect measure of the amount of epitope-binding antibodies in sera (FIG. 1).

FLAG-Fabs were purified [10] and assayed in a FLAG-Fab-specific ELISA to determine the correct concentration to be used in inhibition experiments. Briefly, FLAG-Fab preparations of known concentration were titered by ELISA [11], where antigen-coated plates were blocked for 1 h at 37° C. with PBS/1% BSA. After removing the blocking solution, 50 μl of progressive dilutions of FLAG-Fab made in PBS/BSA 1% were added to the wells and incubated for 2 h at 37° C. Plates were washed 10 times with PBS/0.05% Tween-20 in an automated plate washer (DiaSorin, Saluggia, Italy) before adding 50 μl of a 10 μg/ml solution of anti-FLAG mouse monoclonal antibody M2 (Sigma, St. Louis, Mo.; 10 μg/ml in PBS) in PBS/BSA 1%. After 1 h incubation at 37° C., wells were washed 10 times with PBS/Tween-20 as above and mouse monoclonal antibody binding was revealed with horseradish peroxidase-conjugated goat anti-mouse IgG (Pierce; 1:8,000 in PBS). Substrate was added and plates were read for $OD_{450}$ in an automated plate reader after 30 min incubation at room temperature in the dark. All assays were performed at least in double. A negative control antigen (BSA) was always included and the OD reading was subtracted as background.

For the determination of the Fab Inhibiting Titer (FIT) of sera, a concentration of purified FLAG-Fabs yielding in standard conditions an $OD_{450}$ reading equal to 50% of maximum reading was used for further experiments of Fab inhibition ELISA. For these experiments, plates were coated and blocked as described above. Progressive 1:4 serum dilutions in PBS/BSA 1% were added in the amount of 50 μl per ELISA well. After 2 h of incubation at 37° C., purified FLAG-Fab was added directly to serum dilutions to reach the desired final concentration. Plates were incubated for additional 30 min and then processed as described above for FLAG-Fab ELISA. A positive control sample, containing a 20:1 excess of purified unlabeled Fab, corresponding to 100% inhibition, is included. A negative control sample, containing an excess of a control uncorrelated Fab [12] and corresponding to 0% inhibition, is also included. The final results are determined as % of inhibition with the formula: percent inhibition=100× ($OD_{450}$ of probe FLAG-Fab alone–$OD_{450}$ of probe FLAG-Fab with competing serum)/$OD_{450}$ of probe FLAG-Fab alone.

The highest serum dilution giving more than 70% inhibition of FLAG-Fab binding is considered as the Fab Inhibiting Titer (FIT) for that epitope and for that serum.

Results

The appropriate FLAG-Fab concentration to be employed in the assay is determined for each FLAG-Fab and ranges from 10 μg/ml (e8, e20, e137, e301, e509) to 0.1 μg/ml (e10-B). The amino acid sequences of the light and heavy chains of the various antibodies are given below:

```
e8 HC (SEQ ID NO. 1)
LLEQSGAEVKMPGATVKVSCQSSRYTFTSYGIGWVRQAPGQGLEWMG

WISGYTHETKYAQSFQGRVTMTAETSTGTAYMELRSLRSDDTATYYCA

RDGGGRVVVPPTHLRAFDVWGQGT e8 LC (SEQ ID NO. 2)
MAELTQSPGTLSLSPGERATLSCRASHRVNNNFLAWYQQKPGQAPRLLI

SGASTRATGIPDRFSGSGSGTDFTLTISRLEPDDFAVYYCQQYGDSPLY

SFGQGT e10 HC (SEQ ID NO. 3)
LLESGPGLVKPSQTLSLTCTVSGVSISYGGRGVSYWGWVRQSPGKGLE

WIGHIYYFGDTFYNPSLNNRATISIDSSKNQFSLKLKSVTASDTALYFCA

RSTLQYFDWLLTREAAYSIDFWGQGI e10 LC (SEQ ID NO. 4)
MAELTQSPSFLSASVGDRVTITCRASQGVTILLAWYQQKPGKPPKALIYA

ASSLQSGVPSRFSGSGSDTDFTLTISSLQPEDSATYYCQQLNTYPWTFG

QGT e20 HC (SEQ ID NO: 5)
LLEQSGAEVKKPGSSVKVSCKASGDHYGINWVRQAPGQGLEWMGGIIP

VFGTTTYAQKFQGRATITADDSTGTAFLELTRLTFDDTAVYFCATPHQLH

VLRGGKALSPWDYWGQGT e20 LC (SEQ ID NO: 6)
MAELTQSPATLSVSPGERATLSCRASQSVSSNLAWYQQKRGQAPSLLIY

GTSTRATGIPARFSGSGSGTEFTLTISSLQSEDFAVYYCQQYNDWPSTF

GQGT e137 HC (SEQ ID NO: 7)
LLEQSGSEVKVPGSSLKVSCKTSGGTFSTYTFSWVRQAPGQGLEWMG

GITPIIGIANYARNFQDRVTITADESTSTVYMEVRRLRSEDTAVYYCAKT

SEVTATRGRTFFYSAMDVWGQGT e137 LC (SEQ ID NO: 8)
MAELTQSPSFLSASVGDRVTITCRASQGISNYLAWYQQKPGKAPKLLIYA

ASTLQSGVPSRFSGSGSWTEFTLTISRLQPEDFATYYCQHLNTYPWTFG

QGT e301 HC (SEQ ID NO: 9)
LLEQSGSEVKKPGSSVRVSCTTSGGTLSDYGFNWLRQAPGQGPEWMG

GIIPLFRRTTYGQKFQGRLTITADESTGATYMELSSLRSDDTAVYYCARE

KVSVLTGGKSLHYFEYWGKGT e301 LC (SEQ ID NO: 10)
MAELTQSPATLSVSPGERATLSCRASQSVSSRLAWYQQKRGQAPSLLIY

DTSSRATGVPARFSASGSGTQFTLTISSLQSEDFALYYCQQYNDWPSTF

GQGT e509 HC (SEQ ID NO: 11)
LLEESGAEVKKPGSSVKVSCKTSGDTFRYGITWVRQAPGQGLEWMGQI

MPTFATATYAQRFQGRVTISADESTSTAYLEVRSLRSEDTAVYYCATPR

QVTILRGPKALSPWDYWGQGT e509 LC (SEQ ID NO: 12)
MAELTQSPATLSASPGERASLSCRASQSVSSNLAWYQQKPGQAPRLLIS

GASTRATGVPARFSGSGSGTEFTLTISSLQSEDFAVYYCQQYNNWPPH

FGQGT
```

The nucleotide sequences coding for the Fab fragments listed above are indicated as follows:

```
e8 HC (SEQ ID NO: 13)
CTGCTCGAGCAGTCTGGAGCTGAGGTGAAGATGCCTGGGGCCACAG

TGAAGGTCTCCTGCCAGTCTTCCCGTTACACCTTCACCAGTTACGGT

ATCGGCTGGGTGCGACAGGCCCCTGGACAGGGGCTTGAGTGGATG

GGATGGATCAGCGGATACACCCATGAGACAAAATATGCACAGAGTTT

CCAGGGCAGAGTCACCATGACCGCAGAGACATCCACGGGCACAGCG

TATATGGAGTTGAGGAGCCTGCGGTCTGACGACACGGCCACATATTA

CTGCGCGAGAGATGGAGGAGGGAGGGTGGTAGTGCCGCCTACTCAT

CTACGTGCTTTTGATGTCTGGGGTCAAGGGACG e8 LC (SEQ ID NO: 14)
ATGGCCGAGCTCACCCAGTCTCCAGGCACCCTGTCTTTGTGTCCAGG

GGAAAGAGCCACCCTCTCCTGCAGGGCCAGTCACAGAGTCAATAACA

ACTTCTTAGCCTGGTATCAGCAGAAACCTGGCCAGGCTCCCAGGCTC

CTCATCTCTGGTGCATCTACCAGGGCCACTGGCATCCCAGACAGGTT

CAGTGGCAGTGGGTCTGGAACAGACTTCACTCTCACCATCAGCAGAC

TGGAGCCTGATGATTTTGCAGTTTATTATTGTCAGCAGTATGGTGACT

CACCTCTTTATTCTTTTGGCCAGGGGACC
``` e10 HC (SEQ ID NO: 15)
CTGCTCGAGTCTGGCCCAGGACTGGTGAAGCCTTCACAGACCCTGT
CCCTCACCTGCACCGTCTCCGGTGTCTCCATCAGTTACGGTGGTCGT
GGCGTTTCCTACTGGGGTTGGGTCCGCCAGTCCCCAGGGAAGGGCC
TGGAGTGGATTGGCCACATCTACTACTTTGGAGACACCTTCTACAAC
CCGTCGCTCAACAATCGAGCTACCATATCAATAGACTGATCCAAAAAC
CAGTTCTCCCTCAAGCTCAAGTCTGTGACTGCCTGAGACACGGCCCT
GTATTTCTGTGCCAGGAGCACCCTACAGTATTTTGACTGGTTATTGAC
ACGGGAGGCTGCCTACTCCATTGACTTCTGGGGCCAGGGAATA e10 LC (SEQ ID NO: 16)
ATGGCCGAGCTCACCCAGTCTCCATCCTTCCTGTCTGCATCTGTTGG
AGACCGAGTCACCATCACTTGCCGGGCCAGTCAGGGCGTCACCATT
CTTTTAGCCTGGTATCAGCAAAAGCCAGGGAAACCCCCTAAGGCCCT
GATTTATGCTGCATCGTCTTTGCAAAGTGGGGTCCCATCAAGGTTCA
GCGGCAGTGGTTCTGACACAGATTTCACTCTCACAATCAGCAGCCTA
CAGCCTGAAGATTCTCCAACTTATTACTGTCAACAACTTAACACTTAC
CCGTGGACGTTCGGCCAGGGGACC e20 HC (SEQ ID NO: 17)
CTGCTCGAGCAGTCAGGGGCTGAGGTGAAGAAGCCTGGGTCCTCGG
TGAAGGTCTCCTGCAAGGCTTCTGGAGACCACTATGGTATCAACTGG
GTGCGACAGGCCCCTGGACAAGGGCTGGAGTGGATGGGCGGTATCA
TCCCTGTCTTTGGCACAACTACCTACGCACAGAAGTTCCAGGGCAGA
GCCACCATTACCGCGGACGACTCCACGGGGACGGCCTTTTTGGAGC
TGACCAGACTGACATTTGACGACACGGCCGTCTATTTCTGTGCGACA
CCTCACCAACTGCATGTCCTCCGGGGCGGTAAAGCCCTCTCCCCCT
GGGACTACTGGGGCCAGGGAACC e20 LC (SEQ ID NO: 18)
ATGGCCGAGCTCACCCAGTCTCCAGCCACCCTGTCTGTGTCTCCAGG
GGAAAGAGCCACCCTCTCCTGCAGGGCCAGTCAGAGTGTTAGCAGT
AACTTAGCCTGGTACCAGCAGAAACGTGGCCAGGCTCCCAGTCTCCT
CATCTACGGAACATCTACCAGGGCCACTGGTATCCCAGCCAGGTTCA
GTGGCAGTGGGTCTGGGACAGAGTTCACTCTCACCATCAGCAGCCT
GCAGTCTGAAGATTTTGCAGTTTATTACTGTCAGCAGTATAATGATTG
GCCCTCCACCTTCGGCCAAGGGACA e137 HC (SEQ ID NO: 19)
CTGCTCGAGCAGTCTGGGTCTGAAGTAAAAGTGCCCGGGTCCTCGTT
GAAGGTCTCCTGCAAGACTTCTGGAGGCACGTTCAGCACCTATACTT
TCAGCTGGGTGCGACAGGCCCCTGGACAGGGACTTGAGTGGATGGG
GGGGATCACCCCTATCATTGGCATCGCAAACTACGCACGGAACTTCC
AGGACAGAGTCACCATCACCGCGGACGAATCCACGAGCACGGTCTA
CATGGAGGTGAGGAGGCTGAGATCTGAGGACACGGCCGTATATTATT
GTGCGAAAACTTCGGAAGTAACAGCCACTAGAGGGCGGACTTTCTTC
TACTCCGCTATGGACGTCTGGGGTCAAGGGACC e137 LC (SEQ ID NO: 20)
ATGGCCGAGCTCACCCAGTCTCCATCCTTCCTGTCTGCATCTGTAGG
AGACAGAGTCACCATCACTTGCCGGGCCAGTCAGGGCATAAGCAATT
ATTTAGCCTGGTATCAGCAAAAACCAGGGAAAGCCCCTAAGCTCCTG
ATCTATGCTGCATCCACTTTGCAAAGTGGGGTCCCATCGAGGTTCAG
CGGCAGTGGATCTTGGACAGAATTCACTCTCACAATCAGCCGCCTCC
AGCCTGAAGATTTTGCAACTTATTACTGTCAACACCTTAATACTTACCC
GTGGACGTTCGGCCAAGGGACC e301 HC (SEQ ID NO: 21)
CTGCTCGAGCAGTCTGGGTCTGAGGTGAAGAAACCTGGGTCCTCGG
TGAGGGTCTCGTGCACGACTTCTGGAGGCACCTTGAGCGACTATGGT
TTCAACTGGTTACGACAGGCCCCTGGACAAGGGCCTGAGTGGATGG
GAGGGATCATCCCTTTGTTTCGAAGAACAACCTACGGACAGAAGTTC
CAGGGCAGACTCACCATTACCGCGGACGAGTCCACGGGCGCAACCT
ACATGGAGCTGAGCAGCCTGAGATCTGACGACACGGCCGTCTATTAC
TGTGCGAGAGAGAAAGTTTCGGTCCTCACAGGCGGAAAGTCACTCCA
TTACTTTGAATATTGGGGCAAGGGAACC e301 LC (SEQ ID NO: 22)
ATGGCCGAGCTCACGCAGTCTCCAGCCACCCTGTCTGTGTCTCCAG
GGGAAAGAGCCACCCTCTCCTGCAGGGCCAGTCAGAGTGTTAGCAG
CAGGTTAGCCTGGTACCAGCAGAAACGTGGCCAGGCTCCCAGTCTC
CTCATCTATGACACATCTTCCAGGGCCACTGGTGTCCCAGCCAGGTT
CAGTGCCAGTGGGTCTGGGACGCAGTTCACTCTCACCATCAGCAGC
CTGCAGTCTGAAGATTTTGCACTTTATTACTGTCAGCAGTATAATGATT
GGCCCTCCACCTTCGGCCAAGGGACA e509 HC (SEQ ID NO: 23)
CTGCTCGAGGAGTCTGGGGCTGAGGTGAAGAAGCCAGGGTCCTCGG
TGAAGGTCTCCTGCAAGACTTCTGGAGAGACCTTCAGATATGGTATC
ACGTGGGTGCGACAGGCCCCTGGACAAGGGCTTGAGTGGATGGGAC
AGATCATGCCTACGTTTGCGACAGCAACCTACGCACAGAGGTTCCAG
GGCAGAGTCACGATTTCCGCGGACGAATCCACGAGCACAGCCTACTT
GGAGGTGCGCAGCCTGAGATCTGAAGACACGGCCGTCTATTACTGT
GCGACACCTCGCCAAGTTACTATACTTCGGGGACCTAAAGCCCTCTC
CCCTTGGGACTACTGGGGCCAGGGAACC e509 LC (SEQ ID NO: 24)
ATGGCCGAGCTCACCCAGTCTCCAGCCACCCTGTCTGCGTCTCCAG
GGGAAAGAGCCTCCCTCTCCTGCAGGGCCAGTCAGAGTGTTAGTAG
CAACTTAGCCTGGTACCAGCAGAAACCTGGCCAGGCTCCCAGGCTC
CTCATCTCTGGTGCATCCACCAGGGCCACTGGTGTCCCGGCCAGGT
TCAGTGGCAGTGGGTCTGGGACAGAGTTCACTCTCACCATCAGTAGC
CTGCAGTCTGAAGATTTTGCAGTTTATTACTGTCAGCAGTATAATAAC
TGGCCTCCCCACTTTGGCCAGGGGACC

FLAG-Fab ELISA on purified labeled Fab molecules yields very specific and reproducible results. Determination of FIT is performed on 10 HCV-negative sera; the titer is consistently >1:20, the upper detection limit of our test, indicating that no inhibition occurs in the absence of specific anti-HCV antibodies.

Figure 2A:
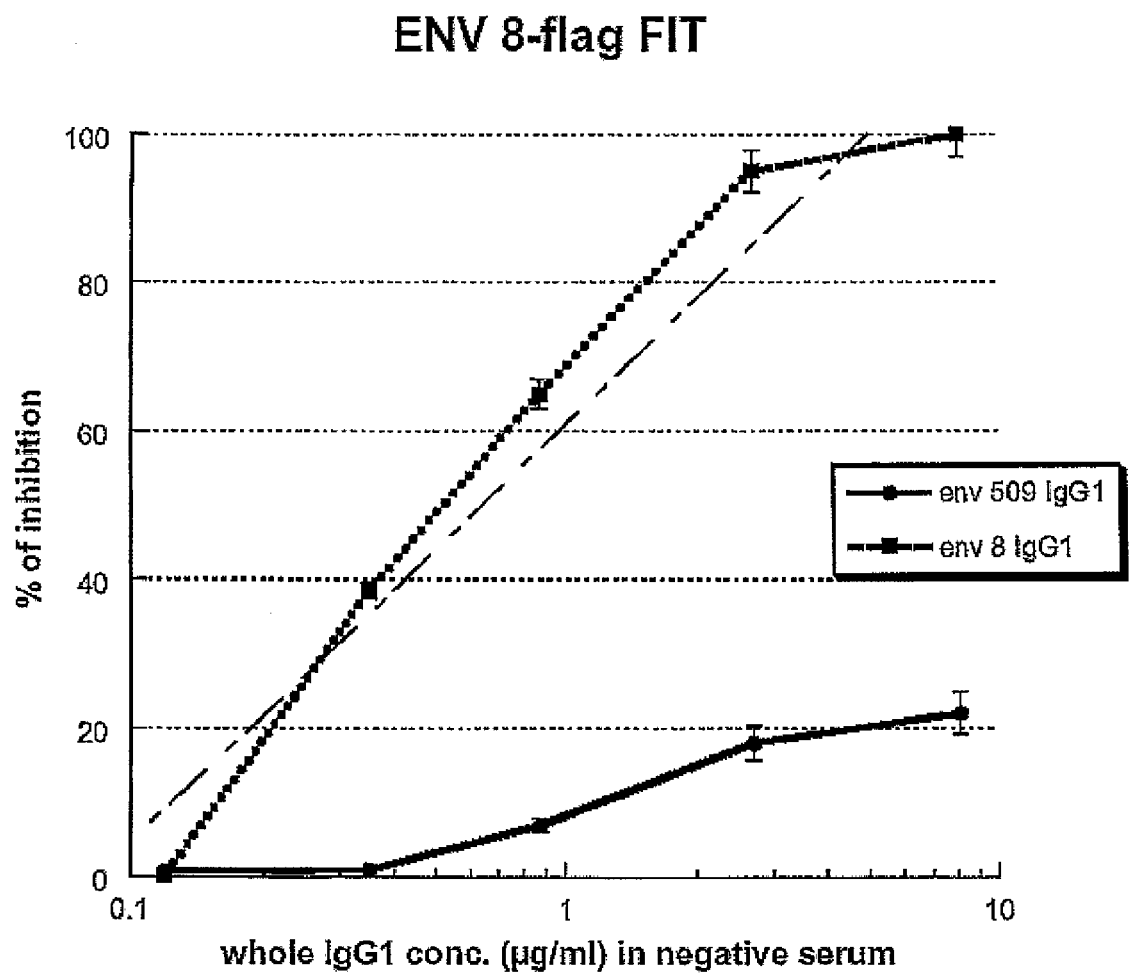
FIGS. 2 A and B: Inhibition of binding between e8-FLAG (A) and e509-FLAG (B) to HCV/E2 by sera containing known concentrations of e8-IgG1 and e509-IgG1 (whole antibodies directed against the epitopes recognized by the Fab). It is clear that the inhibition of Fab binding can be observed only in the presence of the whole antibody having the same specificity and that this depends on antibody concentration.
Figure 2B:
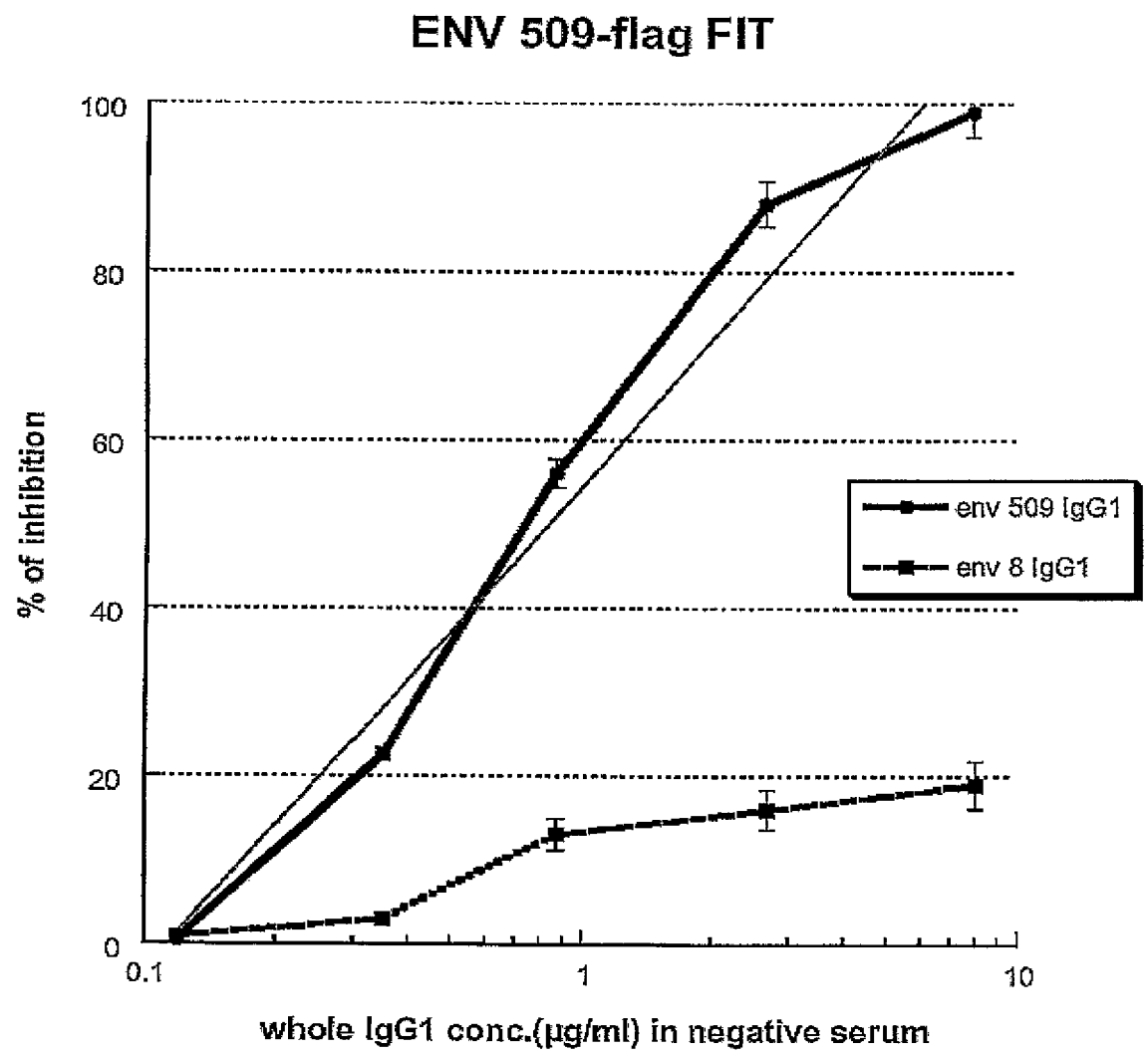

To demonstrate that FIT effectively measures the antibodies directed against epitopes recognized by our FLAG-Fabs, the same analysis is performed on mock specimens prepared by mixing negative sera with human monoclonal antibodies of given specificity, obtaining false samples containing known amounts of IgG directed against the HCV E2 epitopes defined by our Fabs. Results (FIGS. 2A and B) show a good correlation between FIT and antibody amount, indicating that FIT can provide reliable information on the amount of epitope-specific antibodies in a patient's serum.

Finally, FIT is always positive in HCV-positive sera, with values encompassing a wide range of dilutions. FIT is very diverse for the different Fabs in the same serum sample, with considerable heterogeneity between patients.

EXAMPLE 2

Materials and Methods

Human Antibody Fragments

The human recombinant antibody fragments in this example are fully described in Bugli et al. (2001) [7] and correspond to those used in Example 1. Briefly, genes coding for the Fabs were obtained from a phage display combinatorial library containing the IgG1/kappa repertoire of a 58-year-old woman with chronic hepatitis with persistent presence in the blood of HCV RNA of genotype 1b. The genes selected are inserted in an appropriate bacteria expression vector [13] and the transformed cells are then used as a source of recombinant Fabs, which are produced and purified as described [14]. Neutralization of E2 binding to cell (NOB) activity [5, 15] and the reciprocal interactions [7] of these molecules have been described. The presence of similar antibodies in the serum of HCV-infected patients is determined by inhibition ELISA [7].

Pseudotypes and Neutralization Assay

The pseudotypes used here have been fully characterized and described in Matsuura et al., 2001 [8]. Briefly, the VSVΔG*/HCVE1-E2 pseudotype (VSV/HCV) consists of Vesicular Stomatitis Virus, where the G envelope protein is replaced with chimeric E1 and E2HCV envelope glycoproteins consisting of the ectodomains of E1 and E2 proteins of type 1b HCV cDNA clone (NIH-J1) fused to the N-terminal signal sequences, with transmembrane and cytoplasmatic domains of VSV G protein [8]. The construction of plasmids [16], and eukaryotic expression vectors has been described [8, 17]. VSV/HCV is prepared by infecting CHO cells constitutively expressing chimeric E1 and E2 cDNA with a recombinant VSV in which the G protein-coding region has been replaced with the green fluorescent protein gene (GFP) [18]. The VSVΔG*/HCVE1-E2 (VSV/G) pseudotype used as control (and to produce the VSV/HCV pseudotype), is produced by infecting with VSVΔG* a cell line transiently expressing G protein. The neutralization assay is performed as described [8]. Dilutions of purified human recombinant Fabs are incubated with $2.4 \times 10^3$ Infection Units (IU) of the pseudotype VSV/HCV or VSV/G for 30 min at 37° C. and inoculated into HepG2 cells ($4 \times 10^4$ cells) prepared in a 96-well plate. After adsorption for 60 min at 37° C., the cells are washed 3 times with DMEM containing 10% FBS and incubated at 37° C. for 16 hr. The IU of the virus are determined by counting the number of GFP-expressing cells by fluorescence microscopy. Data are presented as percent of inhibition compared with control wells where no antibody was added. Data are the average of three experiments performed in double.

Results

Anti-HCV/E2 Human Monoclonal Antibody Panel Generation and Sequence Characterization The panel of human monoclonal antibody Fab fragments represents the anti-HCV/E2 immune repertoire of a patient with a persistent infection with HCV of genotype 1b [5, 19]. Antibody fragments, selected with purified recombinant HCV/E2 of 1a genotype (strain H)[20] expressed in CHO cells, have been fully characterized and correspond to clones present in the serum of chronically infected patients [7] with a shared equal affinity for HCV/E2. Each of the five antibodies represents one of the five families in which the whole anti-E2 antibody repertoire of this patient is grouped. Fabs belonging to the same family share similar biological activity and have strong homologies of DNA sequences [5]. Each of the five Fabs recognizes a different epitope on the surface of E2 [7]. Divergences from the relative germ-line sequences are typical of antigen-driven affinity maturation (Tables 1a and 1b), suggesting a prolonged exposure to the antigen.

TABLES 1 A, B. Germlines and V gene mutations in variable regions of anti-HCVE2 human monoclonal antibodies.

Sequences are determined as described in Burioni et al., 1998 [5] and aligned with germline sequences in the IMGT database [21]. The percentage of nucleotide and amino acid mutations are calculated according to the Kabat and Wu alignment method [22], taking into account framework region (FR) 1, FR 2 and FR 3 for heavy and light chains, the complementarity determining region (CDR) 1 and CDR 2 for heavy chains, CDR 1, CDR 2 and CDR 3 for light chains.

TABLE 1a

HEAVY CHAINS

| Antibody | V gene | % of mutated nucleotides | | % of mutated amino acids | |
|---|---|---|---|---|---|
| | | FRs | CDRs | FRs | CDRs |
| e 8 | VH1-18 | 9.5 | 22.2 | 14.9 | 33.3 |
| e 20 | VH1-69 | 9.4 | 16.9 | 19 | 38 |
| e 137 | VH1-69 | 11.5 | 15.3 | 14 | 41.7 |
| e 301 | VH1-69 | 8.9 | 19.4 | 15.6 | 45.8 |
| e 509 | VH1-69 | 5.2 | 15.9 | 10.9 | 33.3 |

TABLE 1b

LIGHT CHAINS

| Antibody | V gene | % of mutated nucleotides | | % of mutated amino acids | |
|---|---|---|---|---|---|
| | | FRs | CDRs | FRs | CDRs |
| e 8 | KV 3-20 | 2.7 | 16 | 2.6 | 33.3 |
| e 20 | KV 1-9 | 4.3 | 7.7 | 9.7 | 22.2 |
| e 137 | KV 1-8 | 2.2 | 9 | 3.2 | 15.4 |
| e 301 | KV 3-15 | 3.8 | 14.3 | 9.7 | 23 |
| e 509 | KV 3-15 | 3.2 | 1.3 | 6.5 | 0 |

Neutralizing of binding (NOB) activity of each Fab was also determined [5], with some clones (e137 and e8) found to be unable to inhibit HCV/E2 binding to cells and others inhibiting HCV/E2 binding even at very low concentration (see below).

Neutralization of the Pseudotype Virus by Human Recombinant Fabs

Two of the Fabs, e8 and e20, recognizing different epitopes on the surface of HCV/E2 [7] do not neutralize VSV/HCV pseudotype infection even at high concentrations (80 µg/ml). One of these two Fabs, e20, has strong NOB activity [5], confirming that even antibodies inhibiting E2 binding may fail to prevent viral infection.

Figure 3A:
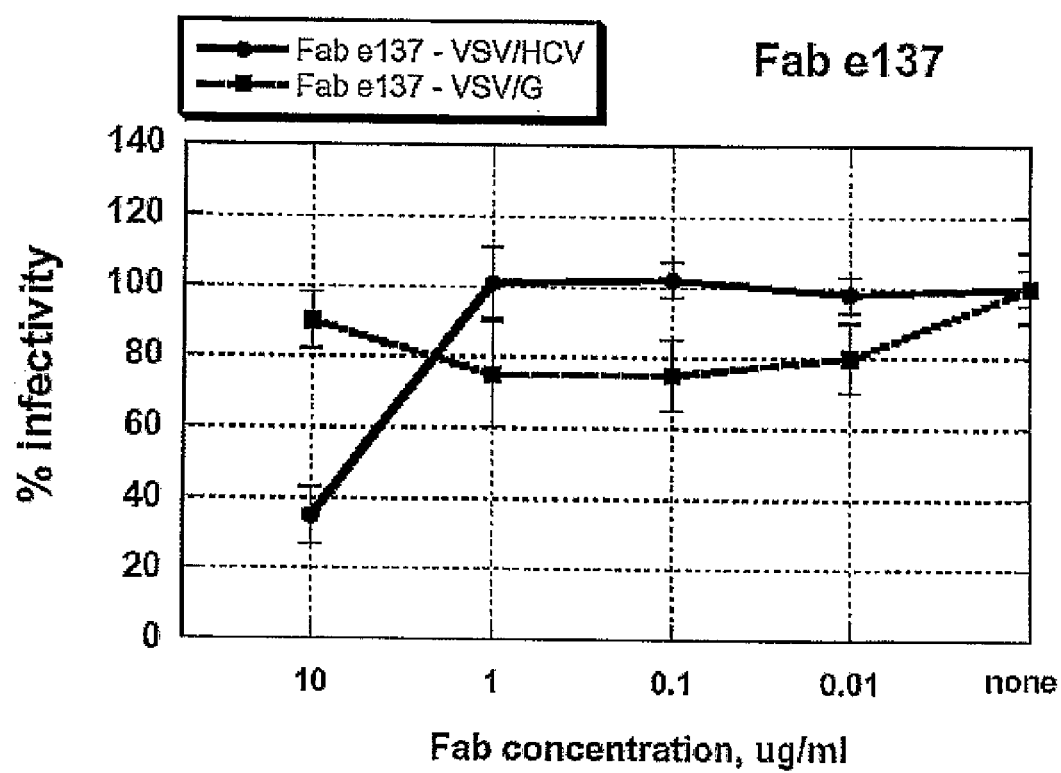
FIGS. 3A, B and C: Inhibition of infection of VSV/HCV and VSV/G pseudotypes by purified anti-HCV/E2 human recombinant Fabs at different concentrations. HepG2 cells infected with Fab-treated pseudotypes were incubated for 16 hr and the number of green fluorescent protein-expressing cells was determined by fluorescence microscopy. Data are presented as % of the infection detected in control wells (no Fabs added). The results shown are the average of three independent assays performed in double.
Figure 3B:
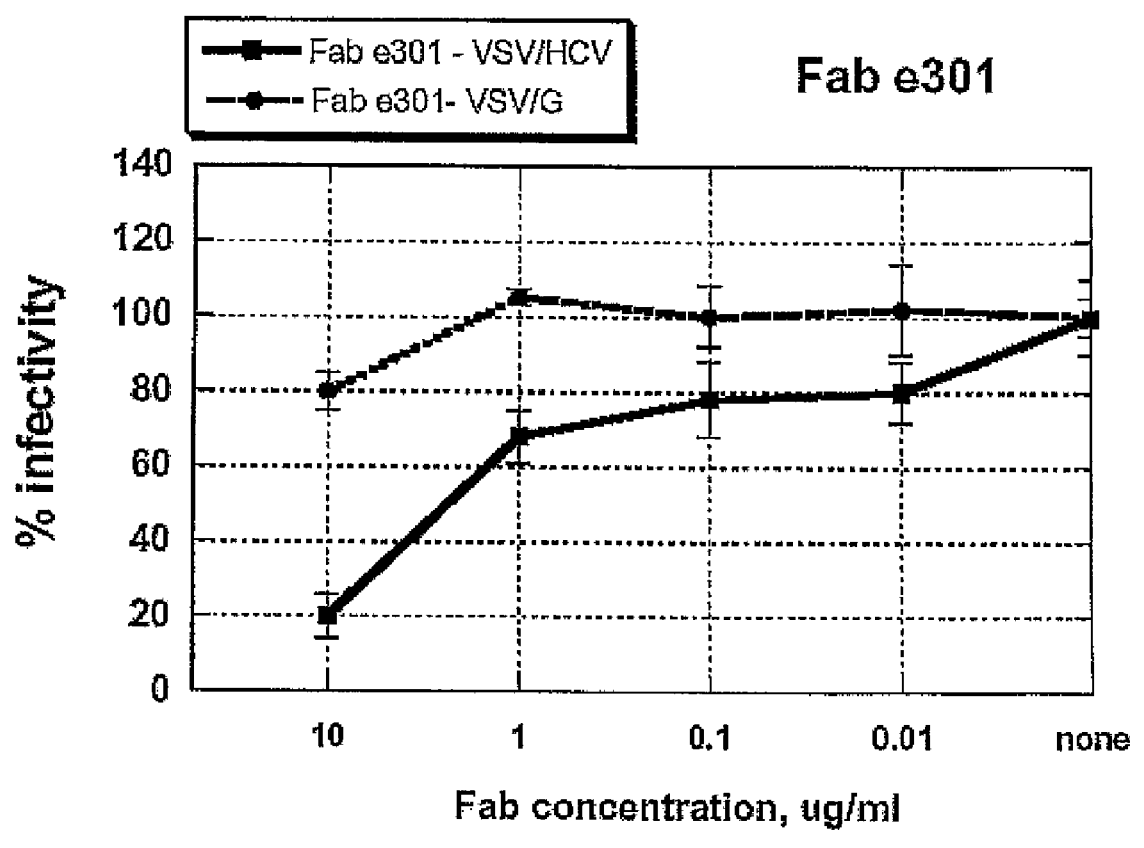
Figure 3C:
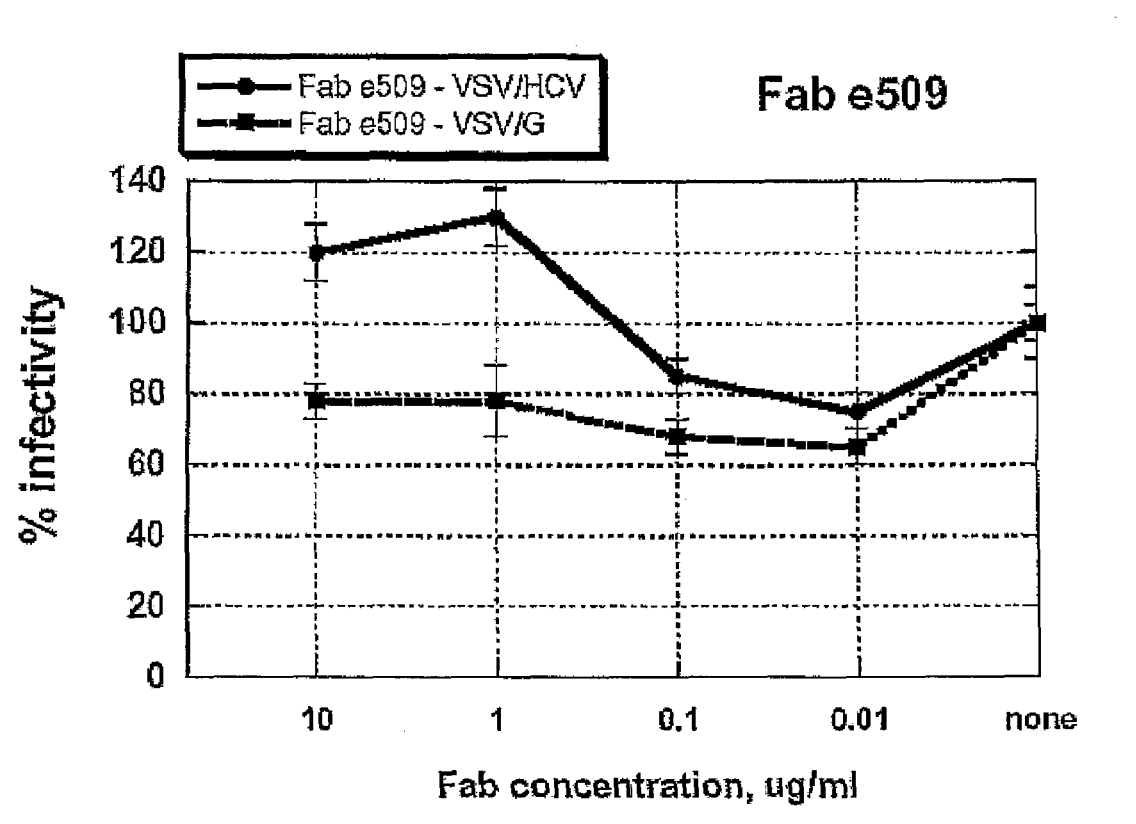
Figure 4:
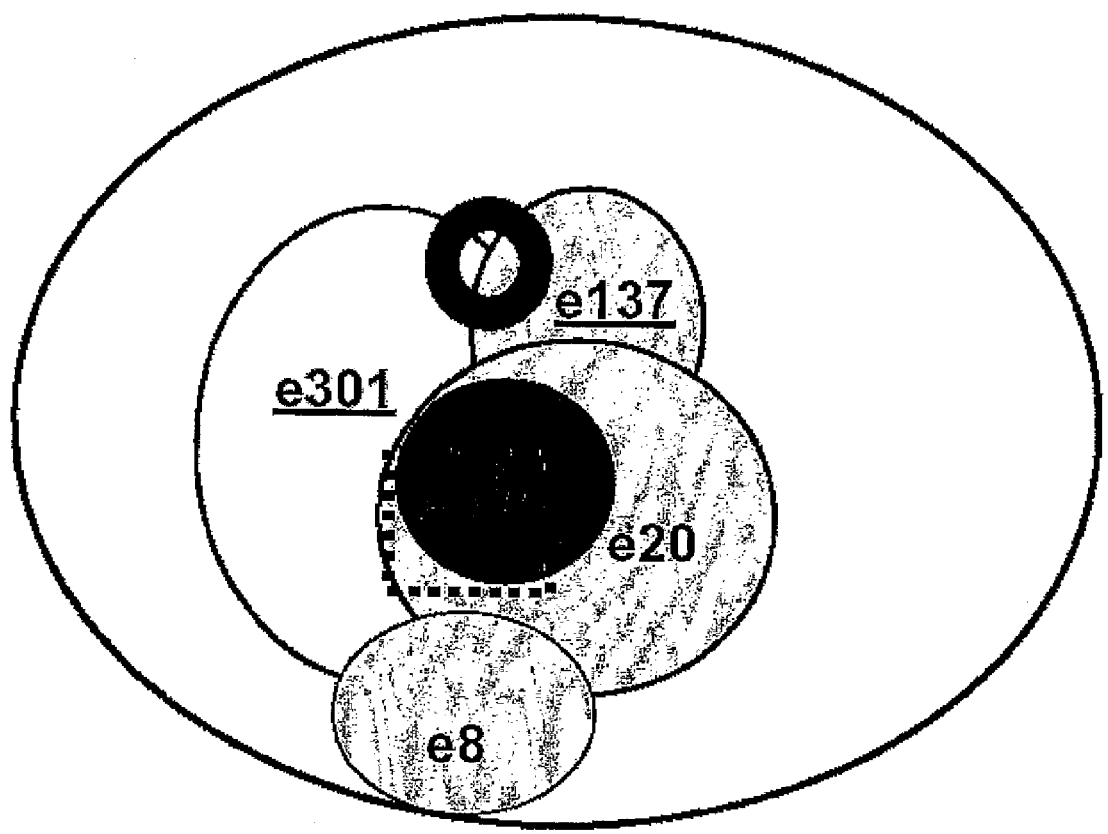
FIG. 4: Two-dimensional surface-like map of the human B cell epitopes present on the surface of HCV/E2 as recognized by the monoclonal antibodies used in this study. Overlapping circles indicate reciprocal inhibition. Fabs endowed with VSV/HCV pseudotype neutralizing activity are underlined. The putative region mediating the interaction of HCV/E2 with the cellular target is indicated by the dotted line. The putative region recognized by neutralizing antibodies is indicated by a solid black circle. Due to modifications that can be induced by antigen-antibody interactions, this diagram does not correspond to the actual physical map.

Two other Fabs, e137 and e301, efficiently neutralize VSV/HCV at a concentration of 10 µg/ml, while VSV pseudotypes bearing the VSV G envelope protein (VSV/G pseudotypes) are not affected (FIGS. 3a and 3b). These data are congruent with previous findings indicating that these two clones compete for the same E2 region, probably recognized by human antibodies endowed with neutralizing activity, as indicated in a two-dimensional surface map of the human epitopes on HCV/E2 (FIG. 4). Fab 509 is currently the strongest available antibody in terms of NOB activity, and is able to inhibit binding between E2 and the cellular target at very low concentrations (Table 2). Incubation of VSV/HCV pseudotypes with this Fab enhance virus entry into hepatoma cells down to a concentration of 1 µg/ml. No increase in infectivity is demonstrated when VSV/G pseudotypes are used, thus ruling out the possibility that a non-specific interaction of this Fab with cellular membrane promotes viral entry into the cell (FIG. 3C).

TABLE 2

Anti-HCV/E2 antibodies characteristics
NOB activity is calculated as the concentration (in µg/ml) achieving 50% of neutralization of binding of a purified HCV/E2 preparation to cellular targets.

| Fab clone | 50% NOB concentration (µg/ml) | Effect on VSV/HCV infection |
|---|---|---|
| e8 | >40 (none) | none |
| e20 | 3 (high) | none |
| e137 | 40 (low) | inhibition |
| e301 | 3 (high) | strong inhibition |
| e509 | <0.035 (highest) | enhancement |

A control antibody [23] exerts no effect on the pseudotype system, as it fails to neutralize both VSV/HCV and VSV/G pseudotypes. The VSV/G pseudotype is duly neutralized by dilutions up to 1:1000 of a polyclonal anti-VSV antiserum used as neutralizing control in these experiments [8], which have no effect on the VSV/HCV. Polyclonal and monoclonal anti-E1 and anti-E2 antibodies raised in several hosts show no neutralizing effect on VSV/HCV pseudotypes.

The neutralizing activity of monovalent Fabs shows that HCV entry can be inhibited without the need for virion aggregation or cross-linking; furthermore, blocking of interaction between the virus and its cellular target seems unlikely to be a key factor in HCV neutralization. These data can explain at the molecular level the lack of correlation between NOB activity in the serum and protection from disease.

Some degree of cross-protection is provided by anti-HCV antibodies, as anti-E2 antibodies selected with E2 of 1a genotype are able to neutralize a pseudotype bearing E2 of 1b genotype.

The results show that Fab 509 is able to enhance the infectivity of the VSV/HCV pseudotype virus, although no effect on the VSV/G construct was apparent. A possible explanation for the ability of e509 to promote viral entry can be found in the observation that this antibody binds specifically and very efficiently to the region of E2 that binds to CD81, a cellular structure involved in viral attachment to the cell [24]. The binding of e509 to E2 could mimic the binding of E2 to one of its cellular targets and promote a modification of E2 conformation similar to the one induced by CD81. E2 is present in at least two conformational states and antibody binding to this protein can modify the sterical status of the protein by modulating the NOB activity of human Fabs without binding competition [6]. Hence, Fab 509 seems to be a key tool for the study of the interactions between HCV and the cell surface and could be used in in vitro models for the evaluation of molecules for vaccines.

This antibody, HCV-Fab-e137, was deposited on 24 Feb. 2009 with DSMZ—Deutsche Sammlung von Mikroorganismen und Zellkulturen GmbH, Inhoffenstr. 7B, 38124 Braunschweig, GERMANY, under the provisions of the Budapest Treaty for the International Recognition of the Deposit of Microorganism for the Purposes of Patent Procedure. HCV-Fab-e137 was accorded DSMZ Accession Number DSM 22321.

This antibody, HCV-Fab-e301, was deposited on 24 Feb. 2009 with DSMZ—Deutsche Sammlung von Mikroorganismen und Zellkulturen GmbH, Inhoffenstr. 7B, 38124 Braunschweig, GERMANY, under the provisions of the Budapest Treaty for the International Recognition of the Deposit of Microorganism for the Purposes of Patent Procedure. HCV-Fab-e301 was accorded DSMZ Accession Number DSM 22322.

REFERENCES

1. Hoofnagle, Hepatitis C: *the clinical spectrum of disease*. Hepatology, 1997. 26(3 Suppl 1): p. 15S-20S.
2. Cerny and Chisari, Pathogenesis of chronic hepatitis C: immunological features of hepatic injury and viral persistence. Hepatology, 1999. 30(3): p. 595-601.
3. Fried and Hoofnagle, *Therapy of hepatitis C*. Semin Liver Dis, 1995. 15(1): p. 82-91.
4. Hoofnagle and di Bisceglie, *The treatment of chronic viral hepatitis*. N Engl J Med, 1997. 336(5): p. 347-56.
5. Burioni, et al., Dissection of human humoral immune response against hepatitis C virus E2 glycoprotein by repertoire cloning and generation of recombinant Fab fragments. Hepatology, 1998. 28(3): p. 810-4.
6. Burioni, et al., Non-neutralizing human antibody fragments against Hepatitis C Virus E2 Glycoprotein Modulate Neutralization of Binding Activity of Human Recombinant Fabs. Virology, 2001. 288: p. 29-35.
7. Bugli, et al., Mapping B cell epitopes of Hepatitis C Virus E2 glycoprotein using human monoclonal antibodies from phage display libraries. J Virol, 2001. 75(20): p. 9986-9990.
8. Matsuura, et al., Characterization of Pseudotype VSV possessing HCV envelope proteins. Virology, 2001. 286(2): p. 263-75.
9. Bender, et al., Recombinant human antibodies: linkage of an Fab fragment from a combinatorial library to an Fc fragment for expression in mammalian cell culture. Hum Antibodies Hybridomas, 1993. 4(2): p. 74-9.
10. Barbas, et al., Human monoclonal Fab fragments derived from a combinatorial library bind to respiratory syncytial virus F glycoprotein and neutralize infectivity. Proc Natl Acad Sci USA, 1992. 89(21): p. 10164-8.
11. Williamson, et al., Human monoclonal antibodies against a plethora of viral pathogens from single combinatorial 12. Burioni, et al., Recombinant human Fab to glycoprotein D neutralizes infectivity and prevents cell-to-cell transmission of herpes simplex viruses 1 and 2 in vitro. Proc Natl Acad Sci USA, 1994. 91(1): p. 355-9.
13. Burioni, et al., A vector for the expression of recombinant monoclonal Fab fragments in bacteria. J Immunol Methods, 1998. 217(1-2): p. 195-9.
14. Barbas, et al., Recombinant human Fab fragments neutralize human type 1 immunodeficiency virus in vitro. Proc Natl Acad Sci USA, 1992. 89(19): p. 9339-43.
15. Rosa, et al., A quantitative test to estimate neutralizing antibodies to the hepatitis C virus: cytofluorimetric assessment of envelope glycoprotein 2 binding to target cells. Proc Natl Acad Sci USA, 1996. 93(5): p. 1759-63.
16. Takikawa, et al., Cell fusion activity of hepatitis C virus envelope proteins. J Virol, 2000. 74(11): p. 5066-74.
17. Ohashi, et al., Ligand-induced activation of chimeric receptors between the erythropoietin receptor and receptor tyrosine kinases. Proc Natl Acad Sci USA, 1994. 91(1): p. 158-62.
18. Takada, et al., A system for functional analysis of Ebola virus glycoprotein. Proc Natl Acad Sci USA, 1997. 94(26): p. 14764-9.
19. Plaisant, et al., Human monoclonal recombinant Fabs specific for HCV antigens obtained by repertoire cloning in phage display combinatorial vectors. Res Virol, 1997.148 (2): p. 165-9.
20. Lesniewski, et al., Antibody to hepatitis C virus second envelope (HCV-E2) glycoprotein: a new marker of HCV infection closely associated with viremia. J Med Virol, 1995. 45(4): p. 415-22.
21. Lefranc, et al., IMGT, *the international ImMunoGeneTics database*. Nucleic Acids Res, 1999. 27(1): p. 209-12.
22. Kabat, *Sequences of Proteins of Immunological Interest*. 5th ed. 1991, Bethesda, Md.: U.S. Department of Health and Human Services.
23. Burioni, et al., A new subtraction technique for molecular cloning of rare antiviral antibody specificities from phage display libraries Res Virol, 1998. 149(5): p. 327-30.
24. Pileri, et al., *Binding of hepatitis C virus to CD81*. Science, 1998. 282(5390): p. 938-41.

The invention claimed is:

1. A method comprising administering an amount of an isolated antibody or a functional fragment thereof, the isolated antibody comprising amino acid sequences SEQ ID NO: 7 and SEQ ID NO: 8, effective to inhibit HCV entry into a cell.

2. The method of claim 1, wherein the isolated antibody comprises human monoclonal antibody Fab fragment e137.

3. The method of claim 1 wherein the isolated antibody is a full size human monoclonal antibody.

4. The method of claim 1, wherein the isolated antibody is an IgG1 molecule.

5. The method of claim 1, wherein the isolated antibody or functional fragment thereof is administered in a composition for parenteral use.

6. A method comprising administering an amount of an isolated antibody or a functional fragment thereof, the isolated antibody comprising amino acid sequences SEQ ID NO: 9 and SEQ ID NO: 10, effective to inhibit HCV entry into a cell.

7. The method of claim 6, wherein the isolated antibody comprises human monoclonal antibody Fab fragment e301.

8. The method of claim 6, wherein the isolated antibody is a full size human monoclonal antibody.

9. The method of claim 6, wherein the isolated antibody is an IgG1 molecule.

10. The method of claim 6, wherein the isolated antibody or functional fragment thereof is administered in a composition for parenteral use.

11. A method comprising administering to the subject an effective amount of a first isolated antibody and a second isolated antibody, the first isolated antibody comprising human monoclonal antibody Fab fragment e301 or a functional fragment thereof effective to inhibit HCV entry into a cell, and the second isolated antibody comprising human monoclonal antibody Fab fragment e137 or a functional fragment thereof effective to inhibit HCV entry into a cell.

12. The method of claim 11, wherein the first isolated antibody is human monoclonal antibody Fab fragment e301 or a functional fragment thereof and the second isolated antibody is human monoclonal antibody Feb fragment e137 or a functional fragment thereof.

13. The method of claim 11 wherein at least one of the first isolated antibody and second isolated antibody is a full size human monoclonal antibody.

14. The method of claim 11, wherein at least one of the first isolated antibody and second isolated antibody is an IgG1 molecule.

15. The method of claim 11, wherein the at least one of a first isolated antibody and a second isolated antibody, is administered in a composition for parenteral use.

* * * * *

SEQUENCE LISTING

<160> NUMBER OF SEQ ID NOS: 24

<210> SEQ ID NO 1
<211> LENGTH: 119
<212> TYPE: PRT
<213> ORGANISM: Homo sapiens

<400> SEQUENCE: 1

Leu Leu Glu Gln Ser Gly Ala Glu Val Lys Met Pro Gly Ala Thr Val
1               5                   10                  15

Lys Val Ser Cys Gln Ser Ser Arg Tyr Thr Phe Thr Ser Tyr Gly Ile
            20                  25                  30

Gly Trp Val Arg Gln Ala Pro Gly Gln Gly Leu Glu Trp Met Gly Trp
        35                  40                  45

Ile Ser Gly Tyr Thr His Glu Thr Lys Tyr Ala Gln Ser Phe Gln Gly
    50                  55                  60

Arg Val Thr Met Thr Ala Glu Thr Ser Thr Gly Thr Ala Tyr Met Glu
65                  70                  75                  80

Leu Arg Ser Leu Arg Ser Asp Asp Thr Ala Thr Tyr Tyr Cys Ala Arg
                85                  90                  95

Asp Gly Gly Arg Val Val Val Pro Pro Thr His Leu Arg Ala Phe
            100                 105                 110

Asp Val Trp Gly Gln Gly Thr
        115

<210> SEQ ID NO 2
<211> LENGTH: 104
<212> TYPE: PRT
<213> ORGANISM: Homo sapiens

<400> SEQUENCE: 2

Met Ala Glu Leu Thr Gln Ser Pro Gly Thr Leu Ser Leu Ser Pro Gly
1               5                   10                  15

Glu Arg Ala Thr Leu Ser Cys Arg Ala Ser His Arg Val Asn Asn Asn
            20                  25                  30

```
Phe Leu Ala Trp Tyr Gln Gln Lys Pro Gly Gln Ala Pro Arg Leu Leu
            35                  40                  45

Ile Ser Gly Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65              70                  75                  80

Pro Asp Asp Phe Ala Val Tyr Tyr Cys Gln Gln Tyr Gly Asp Ser Pro
                85                  90                  95

Leu Tyr Ser Phe Gly Gln Gly Thr
                100

<210> SEQ ID NO 3
<211> LENGTH: 124
<212> TYPE: PRT
<213> ORGANISM: Homo sapiens

<400> SEQUENCE: 3

Leu Leu Glu Ser Gly Pro Gly Leu Val Lys Pro Ser Gln Thr Leu Ser
 1               5                  10                  15

Leu Thr Cys Thr Val Ser Gly Val Ser Ile Ser Tyr Gly Gly Arg Gly
             20                  25                  30

Val Ser Tyr Trp Gly Trp Val Arg Gln Ser Pro Gly Lys Gly Leu Glu
            35                  40                  45

Trp Ile Gly His Ile Tyr Tyr Phe Gly Asp Thr Phe Tyr Asn Pro Ser
 50                  55                  60

Leu Asn Asn Arg Ala Thr Ile Ser Ile Asp Ser Ser Lys Asn Gln Phe
 65                  70                  75                  80

Ser Leu Lys Leu Lys Ser Val Thr Ala Ser Asp Thr Ala Leu Tyr Phe
                85                  90                  95

Cys Ala Arg Ser Thr Leu Gln Tyr Phe Asp Trp Leu Leu Thr Arg Glu
            100                 105                 110

Ala Ala Tyr Ser Ile Asp Phe Trp Gly Gln Gly Ile
            115                 120

<210> SEQ ID NO 4
<211> LENGTH: 102
<212> TYPE: PRT
<213> ORGANISM: Homo sapiens

<400> SEQUENCE: 4

Met Ala Glu Leu Thr Gln Ser Pro Ser Phe Leu Ser Ala Ser Val Gly
 1               5                  10                  15

Asp Arg Val Thr Ile Thr Cys Arg Ala Ser Gln Gly Val Thr Ile Leu
             20                  25                  30

Leu Ala Trp Tyr Gln Gln Lys Pro Gly Lys Pro Pro Lys Ala Leu Ile
            35                  40                  45

Tyr Ala Ala Ser Ser Leu Gln Ser Gly Val Pro Ser Arg Phe Ser Gly
 50                  55                  60

Ser Gly Ser Asp Thr Asp Phe Thr Leu Thr Ile Ser Ser Leu Gln Pro
 65                  70                  75                  80

Glu Asp Ser Ala Thr Tyr Tyr Cys Gln Gln Leu Asn Thr Tyr Pro Trp
                85                  90                  95

Thr Phe Gly Gln Gly Thr
                100

<210> SEQ ID NO 5
```

```
<211> LENGTH: 116
<212> TYPE: PRT
<213> ORGANISM: Homo sapiens

<400> SEQUENCE: 5

Leu Leu Glu Gln Ser Gly Ala Glu Val Lys Lys Pro Gly Ser Ser Val
1               5                   10                  15

Lys Val Ser Cys Lys Ala Ser Gly Asp His Tyr Gly Ile Asn Trp Val
            20                  25                  30

Arg Gln Ala Pro Gly Gln Gly Leu Glu Trp Met Gly Gly Ile Ile Pro
        35                  40                  45

Val Phe Gly Thr Thr Thr Tyr Ala Gln Lys Phe Gln Gly Arg Ala Thr
50                  55                  60

Ile Thr Ala Asp Asp Ser Thr Gly Thr Ala Phe Leu Glu Leu Thr Arg
65                  70                  75                  80

Leu Thr Phe Asp Asp Thr Ala Val Tyr Phe Cys Ala Thr Pro His Gln
                85                  90                  95

Leu His Val Leu Arg Gly Gly Lys Ala Leu Ser Pro Trp Asp Tyr Trp
            100                 105                 110

Gly Gln Gly Thr
        115

<210> SEQ ID NO 6
<211> LENGTH: 102
<212> TYPE: PRT
<213> ORGANISM: Homo sapiens

<400> SEQUENCE: 6

Met Ala Glu Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Arg Gly Gln Ala Pro Ser Leu Leu Ile
        35                  40                  45

Tyr Gly Thr Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Ser
                85                  90                  95

Thr Phe Gly Gln Gly Thr
            100

<210> SEQ ID NO 7
<211> LENGTH: 120
<212> TYPE: PRT
<213> ORGANISM: Homo sapiens

<400> SEQUENCE: 7

Leu Leu Glu Gln Ser Gly Ser Glu Val Lys Val Pro Gly Ser Ser Leu
1               5                   10                  15

Lys Val Ser Cys Lys Thr Ser Gly Gly Thr Phe Ser Thr Tyr Thr Phe
            20                  25                  30

Ser Trp Val Arg Gln Ala Pro Gly Gln Gly Leu Glu Trp Met Gly Gly
        35                  40                  45

Ile Thr Pro Ile Ile Gly Ile Ala Asn Tyr Ala Arg Asn Phe Gln Asp
50                  55                  60
```

```
Arg Val Thr Ile Thr Ala Asp Glu Ser Thr Ser Thr Val Tyr Met Glu
 65                  70                  75                  80

Val Arg Arg Leu Arg Ser Glu Asp Thr Ala Val Tyr Tyr Cys Ala Lys
                 85                  90                  95

Thr Ser Glu Val Thr Ala Thr Arg Gly Arg Phe Phe Tyr Ser Ala
            100                 105                 110

Met Asp Val Trp Gly Gln Gly Thr
        115                 120

<210> SEQ ID NO 8
<211> LENGTH: 102
<212> TYPE: PRT
<213> ORGANISM: Homo sapiens

<400> SEQUENCE: 8

Met Ala Glu Leu Thr Gln Ser Pro Ser Phe Leu Ser Ala Ser Val Gly
  1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Trp Thr Glu Phe Thr Leu Thr Ile Ser Arg Leu Gln Pro
 65                  70                  75                  80

Glu Asp Phe Ala Thr Tyr Tyr Cys Gln His Leu Asn Thr Tyr Pro Trp
                 85                  90                  95

Thr Phe Gly Gln Gly Thr
            100

<210> SEQ ID NO 9
<211> LENGTH: 118
<212> TYPE: PRT
<213> ORGANISM: Homo sapiens

<400> SEQUENCE: 9

Leu Leu Glu Gln Ser Gly Ser Glu Val Lys Lys Pro Gly Ser Ser Val
  1               5                  10                  15

Arg Val Ser Cys Thr Thr Ser Gly Gly Thr Leu Ser Asp Tyr Gly Phe
                 20                  25                  30

Asn Trp Leu Arg Gln Ala Pro Gly Gln Gly Pro Glu Trp Met Gly Gly
             35                  40                  45

Ile Ile Pro Leu Phe Arg Arg Thr Thr Tyr Gly Gln Lys Phe Gln Gly
 50                  55                  60

Arg Leu Thr Ile Thr Ala Asp Glu Ser Thr Gly Ala Thr Tyr Met Glu
 65                  70                  75                  80

Leu Ser Ser Leu Arg Ser Asp Asp Thr Ala Val Tyr Tyr Cys Ala Arg
                 85                  90                  95

Glu Lys Val Ser Val Leu Thr Gly Gly Lys Ser Leu His Tyr Phe Glu
            100                 105                 110

Tyr Trp Gly Lys Gly Thr
            115

<210> SEQ ID NO 10
<211> LENGTH: 102
<212> TYPE: PRT
<213> ORGANISM: Homo sapiens
```

-continued

```
<400> SEQUENCE: 10

Met Ala Glu Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Arg
            20                  25                  30

Leu Ala Trp Tyr Gln Gln Lys Arg Gly Gln Ala Pro Ser Leu Leu Ile
        35                  40                  45

Tyr Asp Thr Ser Ser Arg Ala Thr Gly Val Pro Ala Arg Phe Ser Ala
    50                  55                  60

Ser Gly Ser Gly Thr Gln Phe Thr Leu Thr Ile Ser Ser Leu Gln Ser
65                  70                  75                  80

Glu Asp Phe Ala Leu Tyr Tyr Cys Gln Gln Tyr Asn Asp Trp Pro Ser
                85                  90                  95

Thr Phe Gly Gln Gly Thr
            100

<210> SEQ ID NO 11
<211> LENGTH: 118
<212> TYPE: PRT
<213> ORGANISM: Homo sapiens

<400> SEQUENCE: 11

Leu Leu Glu Glu Ser Gly Ala Glu Val Lys Lys Pro Gly Ser Ser Val
1               5                   10                  15

Lys Val Ser Cys Lys Thr Ser Gly Asp Thr Phe Arg Tyr Gly Ile Thr
            20                  25                  30

Trp Val Arg Gln Ala Pro Gly Gln Gly Leu Glu Trp Met Gly Gln Ile
        35                  40                  45

Met Pro Thr Phe Ala Thr Ala Thr Tyr Ala Gln Arg Phe Gln Gly Arg
    50                  55                  60

Val Thr Ile Ser Ala Asp Glu Ser Thr Ser Thr Ala Tyr Leu Glu Val
65                  70                  75                  80

Arg Ser Leu Arg Ser Glu Asp Thr Ala Val Tyr Tyr Cys Ala Thr Pro
                85                  90                  95

Arg Gln Val Thr Ile Leu Arg Gly Pro Lys Ala Leu Ser Pro Trp Asp
            100                 105                 110

Tyr Trp Gly Gln Gly Thr
        115

<210> SEQ ID NO 12
<211> LENGTH: 102
<212> TYPE: PRT
<213> ORGANISM: Homo sapiens

<400> SEQUENCE: 12

Met Ala Glu Leu Thr Gln Ser Pro Ala Thr Leu Ser Ala Ser Pro Gly
1               5                   10                  15

Glu Arg Ala Ser Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Ser Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
```

His Phe Gly Gln Gly Thr
        100

<210> SEQ ID NO 13
<211> LENGTH: 357
<212> TYPE: DNA
<213> ORGANISM: Homo sapiens

<400> SEQUENCE: 13

| | | | | | |
|---|---|---|---|---|---|
| ctgctcgagc | agtctggagc | tgaggtgaag | atgcctgggg | ccacagtgaa | ggtctcctgc | 60 |
| cagtcttccc | gttacacctt | caccagttac | ggtatcggct | gggtgcgaca | ggcccctgga | 120 |
| caggggcttg | agtggatggg | atggatcagc | ggatacaccc | atgagacaaa | atatgcacag | 180 |
| agtttccagg | gcagagtcac | catgaccgca | gagacatcca | cgggcacagc | gtatatggag | 240 |
| ttgaggagcc | tgcggtctga | cgacacggcc | acatattact | gcgcgagaga | tggaggaggg | 300 |
| agggtggtag | tgccgcctac | tcatctacgt | gcttttgatg | tctggggtca | agggacg | 357 |

<210> SEQ ID NO 14
<211> LENGTH: 312
<212> TYPE: DNA
<213> ORGANISM: Homo sapiens

<400> SEQUENCE: 14

| | | | | | |
|---|---|---|---|---|---|
| atggccgagc | tcacccagtc | tccaggcacc | ctgtctttgt | ctccagggga | aagagccacc | 60 |
| ctctcctgca | gggccagtca | cagagtcaat | aacaacttct | tagcctggta | tcagcagaaa | 120 |
| cctggccagg | ctcccaggct | cctcatctct | ggtgcatcta | ccagggccac | tggcatccca | 180 |
| gacaggttca | gtggcagtgg | gtctggaaca | gacttcactc | tcaccatcag | cagactggag | 240 |
| cctgatgatt | ttgcagttta | ttattgtcag | cagtatggtg | actcacctct | ttattctttt | 300 |
| ggccagggga | cc | | | | | 312 |

<210> SEQ ID NO 15
<211> LENGTH: 372
<212> TYPE: DNA
<213> ORGANISM: Homo sapiens

<400> SEQUENCE: 15

| | | | | | |
|---|---|---|---|---|---|
| ctgctcgagt | ctggcccagg | actggtgaag | ccttcacaga | ccctgtccct | cacctgcacc | 60 |
| gtctccggtg | tctccatcag | ttacggtggt | cgtggcgttt | cctactgggg | ttgggtccgc | 120 |
| cagtccccag | ggaagggcct | ggagtggatt | ggccacatct | actactttgg | agacaccttc | 180 |
| tacaacccgt | ccctcaacaa | tcgagctacc | atatcaatag | actcatccaa | aaaccagttc | 240 |
| tccctcaagc | tcaagtctgt | gactgcctca | gacacggccc | tgtatttctg | tgccaggagc | 300 |
| accctacagt | attttgactg | gttattgaca | cgggaggctg | cctactccat | tgacttctgg | 360 |
| ggccagggaa | ta | | | | | 372 |

<210> SEQ ID NO 16
<211> LENGTH: 306
<212> TYPE: DNA
<213> ORGANISM: Homo sapiens

<400> SEQUENCE: 16

| | | | | | |
|---|---|---|---|---|---|
| atggccgagc | tcacccagtc | tccatccttc | ctgtctgcat | ctgttggaga | ccgagtcacc | 60 |
| atcacttgcc | gggccagtca | gggcgtcacc | attctttag | cctggtatca | gcaaaagcca | 120 |

```
gggaaacccc ctaaggccct gatttatgct gcatcgtctt tgcaaagtgg ggtcccatca      180
aggttcagcg gcagtggttc tgacacagat ttcactctca caatcagcag cctacagcct      240
gaagattctg caacttatta ctgtcaacaa cttaacactt acccgtggac gttcggccag      300
gggacc                                                                306

<210> SEQ ID NO 17
<211> LENGTH: 348
<212> TYPE: DNA
<213> ORGANISM: Homo sapiens

<400> SEQUENCE: 17
ctgctcgagc agtcaggggc tgaggtgaag aagcctgggt cctcggtgaa ggtctcctgc      60
aaggcttctg gagaccacta tggtatcaac tgggtgcgac aggcccctgg acaagggctg      120
gagtggatgg gcggtatcat ccctgtcttt ggcacaacta cctacgcaca gaagttccag      180
ggcagagcca ccattaccgc ggacgactcc acggggacgg cctttttgga gctgaccaga      240
ctgacatttg acgacacggc cgtctatttc tgtgcgacac ctcaccaact gcatgtcctc      300
cggggcggta agccctctc cccctgggac tactggggcc agggaacc                   348

<210> SEQ ID NO 18
<211> LENGTH: 306
<212> TYPE: DNA
<213> ORGANISM: Homo sapiens

<400> SEQUENCE: 18
atggccgagc tcacccagtc tccagccacc ctgtctgtgt ctccagggga aagagccacc      60
ctctcctgca gggccagtca gagtgttagc agtaacttag cctggtacca gcagaaacgt      120
ggccaggctc ccagtctcct catctacgga acatctacca gggccactgg tatcccagcc      180
aggttcagtg gcagtgggtc tgggacagag ttcactctca ccatcagcag cctgcagtct      240
gaagattttg cagtttatta ctgtcagcag tataatgatt ggccctccac cttcggccaa      300
gggaca                                                                306

<210> SEQ ID NO 19
<211> LENGTH: 360
<212> TYPE: DNA
<213> ORGANISM: Homo sapiens

<400> SEQUENCE: 19
ctgctcgagc agtctgggtc tgaagtaaaa gtgcccgggt cctcgttgaa ggtctcctgc      60
aagacttctg gaggcacctt cagcacctat actttcagct gggtgcgaca ggcccctgga      120
cagggacttg agtggatggg ggggatcacc cctatcattg gcatcgcaaa ctacgcacgg      180
aacttccagg acagagtcac catcaccgcg gacgaatcca cgagcacggt ctacatggag      240
gtgaggaggc tgagatctga ggacacggcc gtatattatt gtgcgaaaac ttcggaagta      300
acagccacta gagggcggac tttcttctac tccgctatgg acgtctgggg tcaagggacc      360

<210> SEQ ID NO 20
<211> LENGTH: 306
<212> TYPE: DNA
<213> ORGANISM: Homo sapiens

<400> SEQUENCE: 20
atggccgagc tcacccagtc tccatccttc ctgtctgcat ctgtaggaga cagagtcacc      60
atcacttgcc gggccagtca gggcataagc aattatttag cctggtatca gcaaaaacca      120
```

```
gggaaagccc ctaagctcct gatctatgct gcatccactt tgcaaagtgg ggtcccatcg    180
aggttcagcg gcagtggatc ttggacagaa ttcactctca caatcagccg cctccagcct    240
gaagattttg caacttatta ctgtcaacac cttaatactt acccgtggac gttcggccaa    300
gggacc                                                              306

<210> SEQ ID NO 21
<211> LENGTH: 354
<212> TYPE: DNA
<213> ORGANISM: Homo sapiens

<400> SEQUENCE: 21
ctgctcgagc agtctgggtc tgaggtgaag aaacctgggt cctcggtgag ggtctcgtgc     60
acgacttctg gaggcacctt gagcgactat ggtttcaact ggttacgaca ggcccctgga    120
caagggcctg agtggatggg agggatcatc cctttgtttc gaagaacaac ctacggacag    180
aagttccagg gcagactcac cattaccgcg gacgagtcca cgggcgcaac ctacatggag    240
ctgagcagcc tgagatctga cgacacggcc gtctattact gtgcgagaga gaaagtttcg    300
gtcctcacag gcggaaagtc actccattac tttgaatatt ggggcaaggg aacc          354

<210> SEQ ID NO 22
<211> LENGTH: 306
<212> TYPE: DNA
<213> ORGANISM: Homo sapiens

<400> SEQUENCE: 22
atggccgagc tcacgcagtc tccagccacc ctgtctgtgt ctccagggga aagagccacc     60
ctctcctgca gggccagtca gagtgttagc agcaggttag cctggtacca gcagaaacgt    120
ggccaggctc ccagtctcct catctatgac acatcttcca gggccactgg tgtcccagcc    180
aggttcagtg ccagtgggtc tgggacgcag ttcactctca ccatcagcag cctgcagtct    240
gaagattttg cactttatta ctgtcagcag tataatgatt ggccctccac cttcggccaa    300
gggaca                                                              306

<210> SEQ ID NO 23
<211> LENGTH: 354
<212> TYPE: DNA
<213> ORGANISM: Homo sapiens

<400> SEQUENCE: 23
ctgctcgagg agtctggggc tgaggtgaag aagccagggt cctcggtgaa ggtctcctgc     60
aagacttctg gagacacctt cagatatggt atcacgtggg tgcgacaggc ccctggacaa    120
gggcttgagt ggatgggaca gatcatgcct acgtttgcga cagcaaccta cgcacagagg    180
ttccagggca gagtcacgat ttccgcggac gaatccacga gcacagccta cttggaggtg    240
cgcagcctga gatctgaaga cacggccgtc tattactgtg cgacacctcg ccaagttact    300
atacttcggg gacctaaagc cctctcccct tgggactact ggggccaggg aacc          354

<210> SEQ ID NO 24
<211> LENGTH: 306
<212> TYPE: DNA
<213> ORGANISM: Homo sapiens

<400> SEQUENCE: 24
atggccgagc tcacccagtc tccagccacc ctgtctgcgt ctccagggga aagagcctcc     60
```

-continued

```
ctctcctgca gggccagtca gagtgttagt agcaacttag cctggtacca gcagaaacct      120
ggccaggctc ccaggctcct catctctggt gcatccacca gggccactgg tgtcccggcc      180
aggttcagtg gcagtgggtc tgggacagag ttcactctca ccatcagtag cctgcagtct      240
gaagattttg cagtttatta ctgtcagcag tataataact ggcctcccca ctttggccag      300
gggacc                                                                 306
```